(12) United States Patent
Torres

(10) Patent No.: US 6,997,069 B1
(45) Date of Patent: Feb. 14, 2006

(54) TOOL FOR EXTRACTION OF WATER SAMPLES

(76) Inventor: Luis R. Torres, 818 Cooper Rd., Chula Vista, CA (US) 91911

( * ) Notice: Subject to any disclaimer, the term of this patent is extended or adjusted under 35 U.S.C. 154(b) by 0 days.

(21) Appl. No.: 10/963,608

(22) Filed: Oct. 14, 2004

(51) Int. Cl.
*G01N 1/12* (2006.01)

(52) U.S. Cl. .................................................. 73/864.51

(58) Field of Classification Search ............. 73/864.51, 73/864.31; 294/68.1, 68.26
See application file for complete search history.

(56) References Cited

U.S. PATENT DOCUMENTS

| | | | |
|---|---|---|---|
| 1,819,058 A | 8/1931 | Arnold, Jr. | |
| 3,853,009 A * | 12/1974 | Sutherland | ................ 73/864.32 |
| 4,123,753 A | 10/1978 | Gravert | |
| 4,597,562 A * | 7/1986 | Joyce | ......................... 254/334 |
| 5,408,890 A | 4/1995 | Klaus | |
| 6,666,085 B1 | 12/2003 | Lowe | |
| 2004/0188558 A1 * | 9/2004 | Moon et al. | ............. 242/403.1 |

* cited by examiner

*Primary Examiner*—Hezron Williams
*Assistant Examiner*—Paul M. West
(74) *Attorney, Agent, or Firm*—Richard C. Litman

(57) ABSTRACT

A portable reel device for extraction of water samples from feed water storage tanks and the like. The reel incorporates a receptacle known in the art as a thiever. A chain has one end attached to the thiever. The other end of the chain is attached to a spindle. A handle is mounted to one end of the reel for rotating the spindle. A holder is mounted to the other end of the reel, which holder is sized to receive and support the thiever therein. The reel has a base portion for enhancing stability when the reel is disposed on a planar surface.

11 Claims, 4 Drawing Sheets

TOOL FOR EXTRACTION OF WATER SAMPLES

BACKGROUND OF THE INVENTION

1. Field of the Invention

The present invention generally relates to retrieving apparatus. More specifically, the present invention is drawn to a portable device utilized to extract sample water from the tank of a boiler feed water system or the like.

2. Description of the Related Art

When generating steam for running turbines or the like in power plants or on ships, it is important that the quality of the boiler feed water is maintained. Factors such as salinity, chloride content, etc., if not controlled, can cause undo erosion of the boiler and/or turbine surfaces. When at sea, the quality of potable water must also be maintained. To insure consistent water quality, constant monitoring is imperative. Monitoring is usually accomplished by sampling and testing the water supply. Heretofore, water samples have been retrieved by lowering a receptacle known in the art as a thiever into a tank. A chain was attached to the thiever and the sample was lowered into the tank and brought up hand-over-hand. In some instances the thiever was attached to a sounding tape reel. Both of the above scenarios have proven to be tedious and clumsy in that the potential for sample contamination and spillage is great. The art would certainly welcome a portable system, which system would obviate all of the above noted deficiencies.

The systems disclosed in the related art and cited in the IDS art are either not portable, of relatively complicated design or not adapted to retrieve samples.

None of the cited inventions and patents, taken either singly or in combination, is seen to disclose a tool for the extraction of water samples as will subsequently be described and claimed in the instant invention.

SUMMARY OF THE INVENTION

The present invention is a portable reel device for extraction of water samples from feed water storage tanks and the like. The reel incorporates a receptacle known in the art as a thiever. A chain has one end attached to the thiever. The other end of the chain is attached to a spindle. A handle is mounted to one end of the reel for rotating the spindle. A holder is mounted to the other end of the reel, which holder is sized to receive and support the thiever therein. The reel has a base portion for enhancing stability when the reel is disposed on a planar surface.

Accordingly, the instant invention presents a portable device that is utilized to efficiently extract a water sample from feed water tanks. The device functions to diminish the possibility of contamination and spillage of the extracted sample.

The invention provides for improved elements and arrangements thereof for the purposes described which are inexpensive, dependable and fully effective in accomplishing their intended purposes.

A clear understanding of the present invention will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENT

Figure 1:
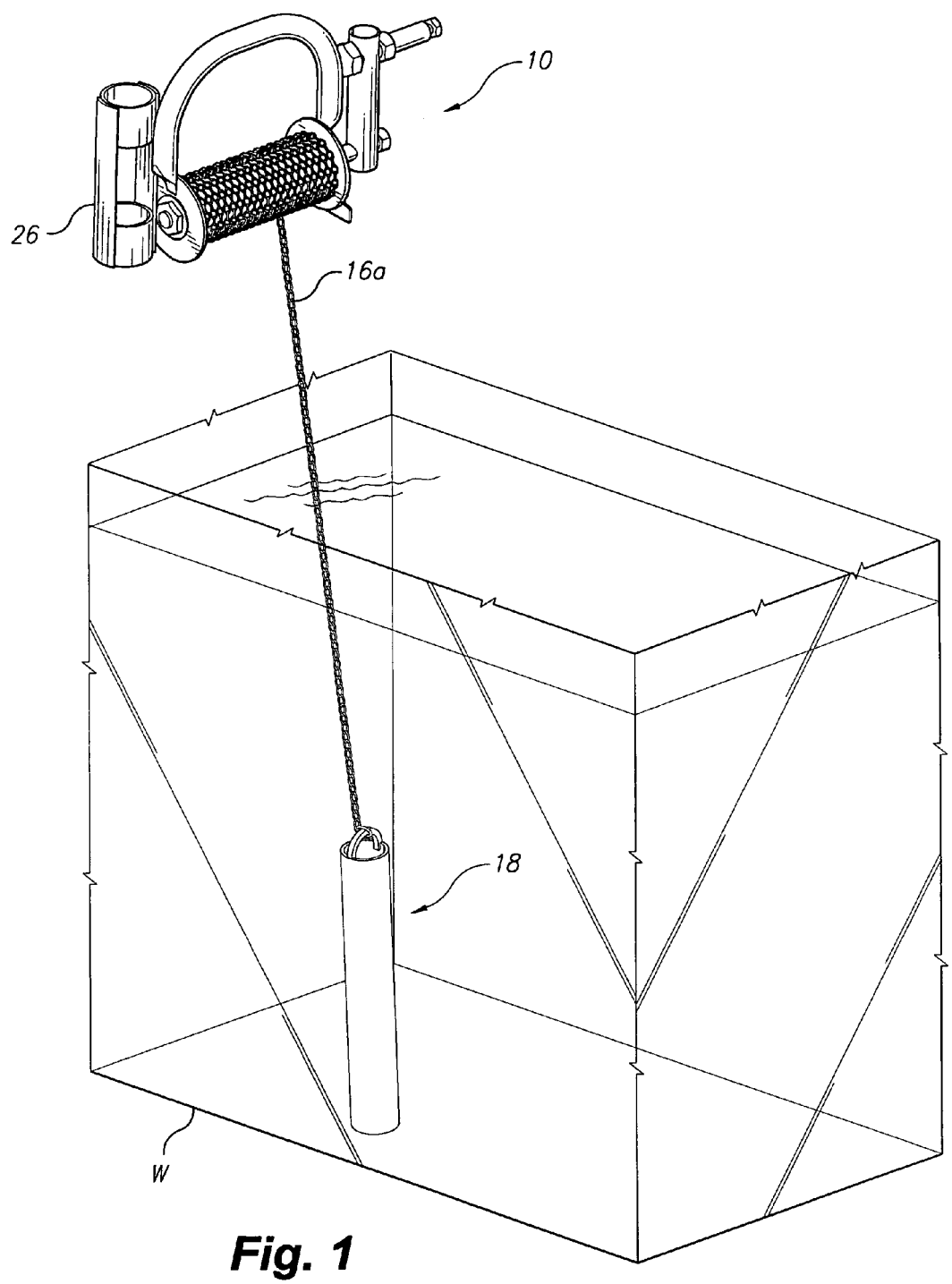
FIG. 1 is an environmental, perspective view of a device for extraction of water samples according to the present invention.

The device of the present invention, generally indicated at 10 in FIG. 1, is employed to extract sample water from a water-holding tank W. As indicated above, tank W may function as a repository for feed water to be fed to a boiler in a power plant or ocean-going vessel or the tank may contain potable water.

Figure 2:
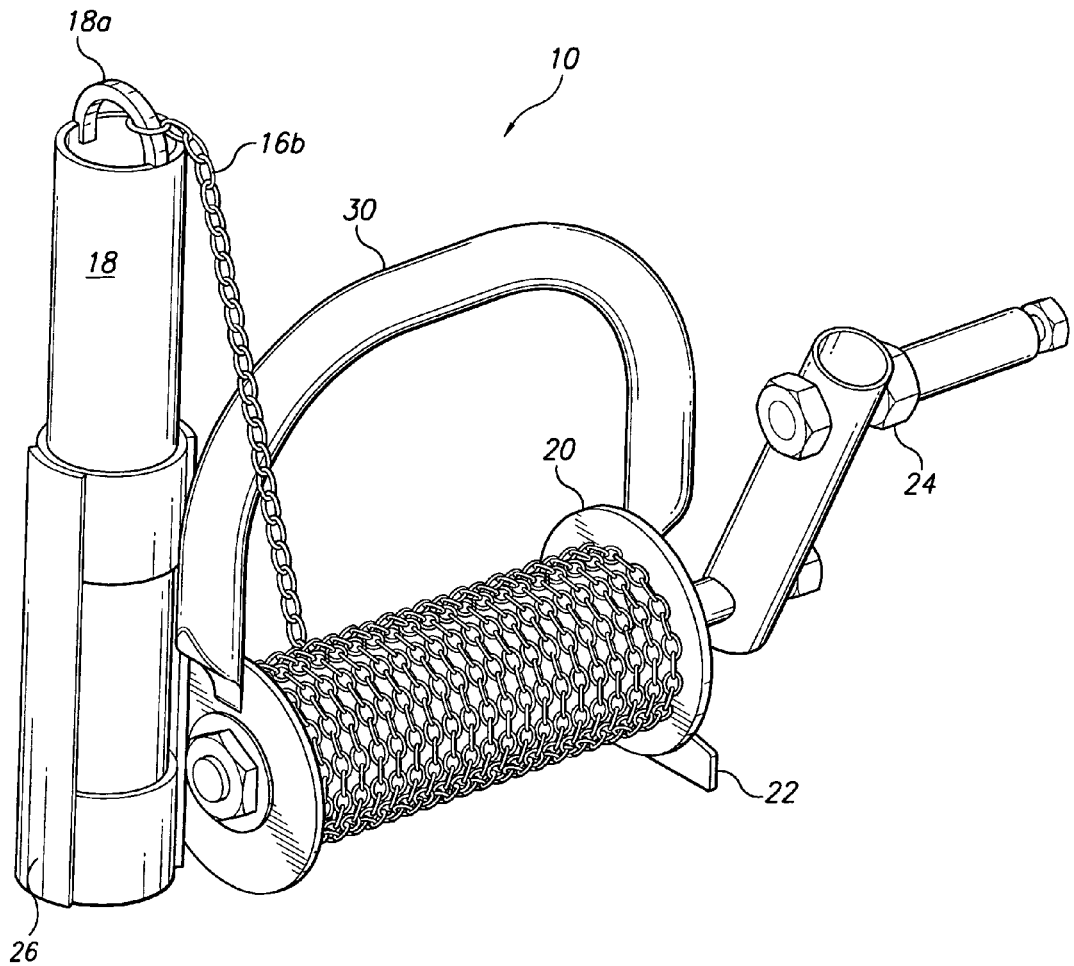
FIG. 2 is a perspective view of a device for extraction of water samples according to the present invention.
Figure 3:
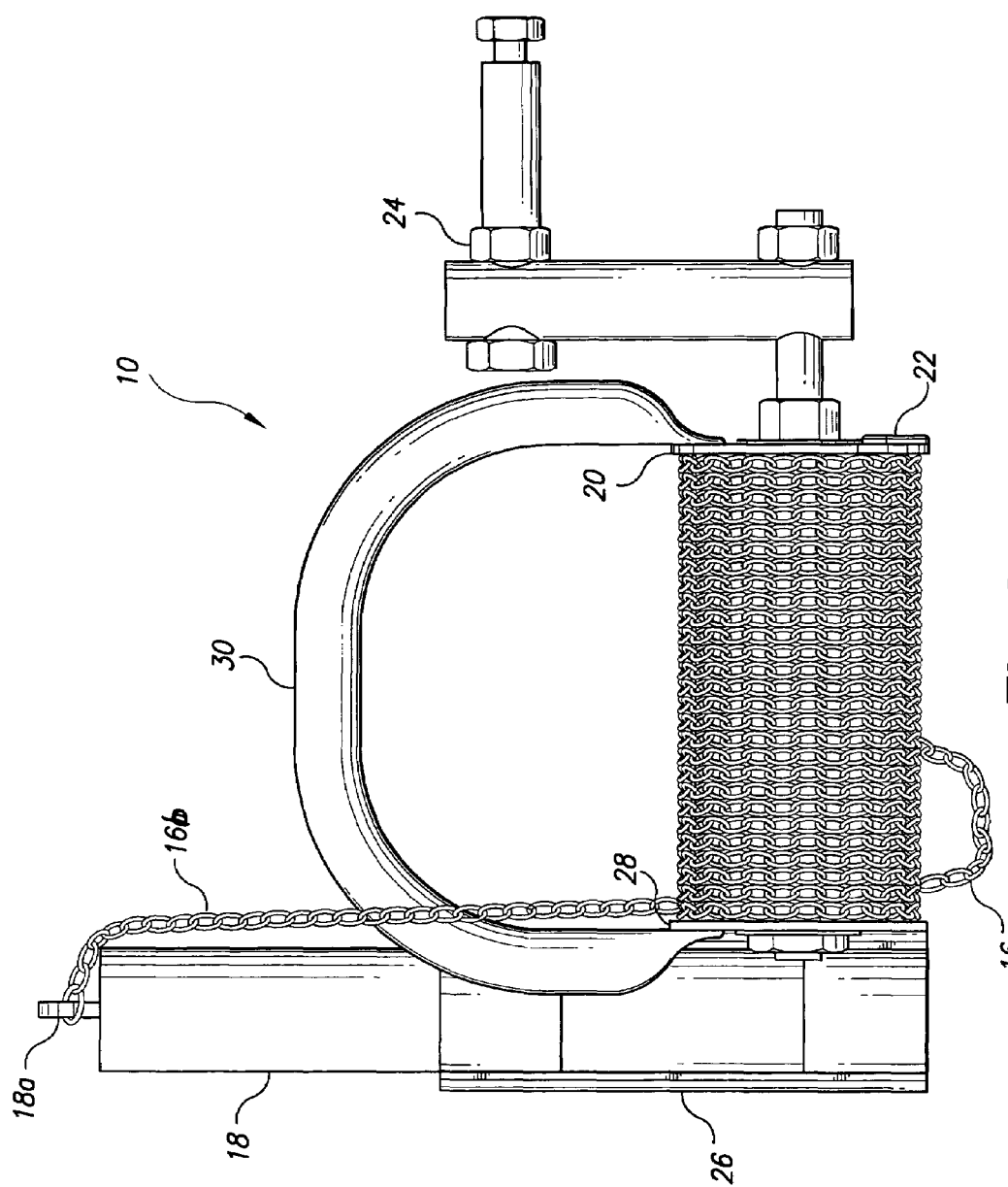
FIG. 3 is a rear view of a device for extraction of water samples according to the present invention.
Figure 4:
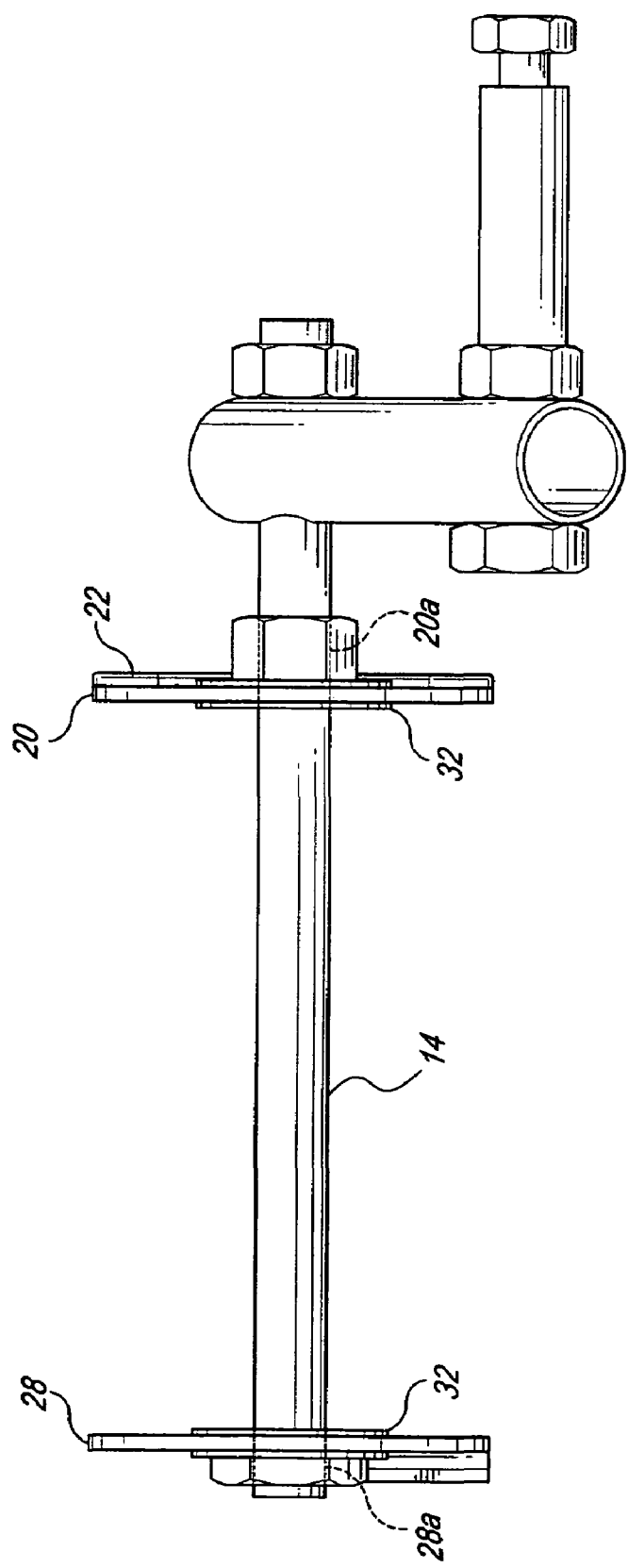
FIG. 4 is a plan view of a turning shaft for extraction of water samples according to the present invention.

As best seen in FIGS. 2–4, device 10 comprises a reel having a rotatable spindle 14 mounted thereon. A chain 16 has a proximate end 16a attached to the spindle 14. The distal end 16b of the chain is attached to an upper member 18a of thiever 18. A first plate 20 defines one side of the reel. Plate 20 has an opening 20a therein to receive an end of the axle of spindle 14. The bottom of plate 20 terminates in a foot 22, which foot provides stable support for the reel. A turning handle 24 is attached to the spindle for manual rotation thereof. A thiever holder 26 is attached to a second plate 28 of the reel. Second plate 28 is also provided with an opening 28a for receiving an axle end of spindle 14. Holder 26 is configured and sized to receive and support the thiever 18 therein. Both thiever 18 and holder 26 are cylindrical as shown. It should be noted, however that both members could be configured in other complimentary shapes if desired. The bottom of holder 26 functions as a stable support base for the reel. A carrying handle 30 spans and is attached to plates 20 and 28. Carrying handle 30 enhances the portability of the device. As best seen in FIG. 4, washers 32 are provided to enhance the rotatable movement of spindle 14. Although stainless steel is preferred, all parts of the device may be fabricated from any suitable, rust-resistant material.

In use, the device is hand-carried to the location (tank) where a sample is to be taken. Thiever 18 is removed from holder 26 and handle 24 is manipulated to unwind chain 16 and lower the thiever into the tank. When a sample has been captured in the thiever, the chain is rewound to retrieve the sample-filled thiever. The thiever is then placed in holder 26. The entire device can now be tipped to empty the sample into a sample bottle or other test container.

It is to be understood that the present invention is not limited to the embodiment described above, but encompasses any and all embodiments within the scope of the following claims.

I claim:

1. A device for extraction of water samples, comprising:
    a portable reel;
    a carrying handle attached to said reel;
    a rotatable spindle mounted on said reel;
    a winding chain, said chain having a proximate end and a distal end, wherein said proximate end is attached to said spindle;
    a thiever, said thiever having an external form, said distal end of said chain attached to said thiever; and
    a holder mounted to said reel, said holder defining an internal form, said internal form being designed and configured to substantially conform to said external surface of said thiever;

wherein said thiever is removably retained in said holder for storage and transport.

2. The device for extraction of water samples as recited in claim 1, further including:
a turning handle attached to said spindle, whereby said spindle may be rotated.

3. The device for extraction of water samples as recited in claim 1, wherein said reel includes a first plate member having an opening therein, said opening receiving a first axle end of the spindle.

4. The device for extraction of water samples as recited in claim 3, wherein said reel includes a second plate member spaced from said first plate member, said second plate member having an opening therein, said opening receiving a second axle end of the spindle.

5. The device for extraction of water samples as recited in claim 1, wherein said spindle, said winding chain, said thiever and said holder are fabricated from stainless steel.

6. A device for extraction of water samples, comprising:
a portable reel;
a carrying handle attached to said reel;
a rotatable spindle mounted on said reel;
a winding chain, said chain having a proximate end and a distal end, wherein said proximate end is attached to said spindle;
a thiever, said thiever having an external form, said distal end of said chain attached to said thiever;
a first plate member defining one side of said reel, said first plate member having an opening therein, said opening receiving a first axle end of the spindle;
a handle for rotating said spindle, said handle attached to said first axle end; and
a holder mounted to said reel, said holder defining an internal form, said internal form being designed and configured to substantially conform to said external surface of said thiever;
wherein said thiever is removably retained in said holder for storage and transport.

7. The device for extraction of water samples as recited in claim 6, wherein said first plate member has a bottom and a foot member defines said bottom.

8. The device for extraction of water samples as recited in claim 6, wherein said reel includes a second plate member spaced from said first plate member, said second plate member having an opening therein, said opening receiving a second axle end of the spindle.

9. A device for extraction of water samples, comprising:
a portable reel;
a rotatable spindle mounted on said reel;
a winding chain, said chain having a proximate end and a distal end, wherein said proximate end is attached to said spindle;
a thiever, said thiever having an external form, said distal end of said chain attached to said thiever;
a first plate member defining one side of said reel, said first plate member having an opening therein and a bottom, said opening receiving a first axle end of the spindle;
a foot member defining the bottom of said first plate member;
a second plate member spaced from said first plate member, said second plate member having an opening therein, said opening receiving a second axle end of the spindle;
a carrying handle attached to said reel; and
a holder mounted to said second plate member, said holder defining an internal form, said internal form being designed and configured to substantially conform to said external surface of said thiever;
wherein said thiever is removably retained in said holder for storage and transport.

10. The device for extraction of water samples as recited in claim 9 including, a turning handle for rotating said spindle, said handle attached to said first axle end.

11. The device for extraction of water samples as recited in claim 9, wherein said carrying handle is attached to said first plate and said second plate.

* * * * *